(12) United States Patent
Dunlop et al.

(10) Patent No.: US 7,763,457 B2
(45) Date of Patent: Jul. 27, 2010

(54) HIGH PHOTOEFFICIENCY MICROALGAE BIOREACTORS

(75) Inventors: Eric H. Dunlop, Paradise (AU); David A. Hazlebeck, El Cajon, CA (US)

(73) Assignee: General Atomics, San Diego, CA (US)

( * ) Notice: Subject to any disclaimer, the term of this patent is extended or adjusted under 35 U.S.C. 154(b) by 606 days.

(21) Appl. No.: 11/549,552

(22) Filed: Oct. 13, 2006

(65) Prior Publication Data
US 2008/0086939 A1    Apr. 17, 2008

(51) Int. Cl.
*C12M 1/00* (2006.01)
(52) U.S. Cl. .............. 435/289.1; 435/293.1; 435/257.1; 435/294.1; 47/1.4
(58) Field of Classification Search .............. 435/292.1, 435/293.1; 47/1.4; 210/606; 366/338
See application file for complete search history.

(56) References Cited

U.S. PATENT DOCUMENTS

| | | | |
|---|---|---|---|
| 2,658,310 A | 11/1953 | Cook | |
| 2,732,661 A | 1/1956 | Spoehr et al. | |
| 2,732,663 A * | 1/1956 | Dewey, II | ..................... 47/1.4 |
| 2,854,792 A | 10/1958 | Juda | |
| 2,949,700 A | 8/1960 | Kathrein | |
| 3,108,402 A | 10/1963 | Kathrein | |
| 3,195,271 A | 7/1965 | Golueke et al. | |
| 3,218,758 A | 11/1965 | Konikoff | |
| 3,446,488 A | 5/1969 | Mail et al. | |
| 3,468,057 A | 9/1969 | Buisson et al. | |
| 3,521,400 A | 7/1970 | Ort | |
| 3,839,198 A * | 10/1974 | Shelef | ......................... 210/602 |
| 3,955,318 A | 5/1976 | Hulls | |
| 3,958,364 A | 5/1976 | Schenck et al. | |
| 4,236,349 A | 12/1980 | Ramus | |
| 4,253,271 A * | 3/1981 | Raymond | ..................... 47/1.4 |
| 4,417,415 A | 11/1983 | Cysewski et al. | |
| 4,732,585 A * | 3/1988 | Lerner | ......................... 95/221 |
| 4,958,460 A | 9/1990 | Nielson et al. | |
| 5,330,913 A | 7/1994 | Nakayama | |
| 5,951,875 A | 9/1999 | Kanel et al. | |
| 6,000,551 A | 12/1999 | Kanel et al. | |
| 6,524,486 B2 | 2/2003 | Borodyanski et al. | |
| 6,667,171 B2 | 12/2003 | Bayless et al. | |
| 2007/0048848 A1* | 3/2007 | Sears | ......................... 435/134 |

OTHER PUBLICATIONS

NREL/TP-580-24190, A Look Back at the U.S. Department of Energy's Aquatic Species Program; Biodiesel from Algae, Jul. 1998.

* cited by examiner

*Primary Examiner*—William H Beisner
*Assistant Examiner*—Michael Hobbs
(74) *Attorney, Agent, or Firm*—Nydegger & Associates

(57) ABSTRACT

A system and method are provided for growing algae with improved photoefficiency. The system includes a bioreactor formed with a conduit for growing algae cells in a medium. Further, the system is provided with a paddle wheel for moving the medium through the conduit at a predetermined fluid flow velocity. In order to ensure that algae cells are efficiently converting light energy to chemical energy, a plurality of barriers is positioned in the fluid stream. Specifically, the barriers are separated by predetermined distances to create von Karman vortices in the medium. As a result, algae cells are sequentially flowed to the surface of the fluid stream to receive light energy for predetermined intervals of time.

11 Claims, 1 Drawing Sheet

HIGH PHOTOEFFICIENCY MICROALGAE BIOREACTORS

FIELD OF THE INVENTION

The present invention pertains generally to the growth of algae cells via photosynthesis. More particularly, the present invention pertains to the treatment of fluid streams holding algae cells to maximize algae cell growth. The present invention is particularly, but not exclusively, useful as a system and method for ensuring high photoefficiency by algae cells in a fluid stream to maximize algae cell growth.

BACKGROUND OF THE INVENTION

As worldwide petroleum deposits decrease, there is rising concern over shortages and the costs that are associated with the production of hydrocarbon products. As a result, alternatives to products that are currently processed from petroleum are being investigated. In this effort, biofuel such as biodiesel has been identified as a possible alternative to petroleum-based transportation fuels. In general, biodiesel is a biofuel comprised of mono-alkyl esters of long chain fatty acids derived from plant oils or animal fats. In industrial practice, biodiesel is created when plant oils or animal fats are reacted with an alcohol, such as methanol.

For plant-derived biofuel, solar energy is first transformed into chemical energy through photosynthesis. The chemical energy is then refined into a usable fuel. Currently, the process involved in creating biofuel from plant oils is expensive relative to the process of extracting and refining petroleum. It is possible, however, that the cost of processing a plant-derived biofuel could be reduced by maximizing the rate of growth of the plant source. Because algae is known to be one of the most efficient plants for converting solar energy into cell growth, it is of particular interest as a biofuel source. Importantly, the use of algae as a biofuel source presents no exceptional problems, i.e., biofuel can be processed from oil in algae as easily as from oils in land-based plants.

While algae transforms solar energy into chemical energy more efficiently than other plants, large-scale algae harvest operations do not optimize photoefficiency for algae in a cost effective manner. For instance, enclosed systems are expensive due to the energy costs invested in providing light energy to the algae. On the other hand, outdoor raceway systems offer poor access to light energy for most of their algae. Specifically, algae near the surface grow densely and block the solar energy from reaching algae deeper in the stream. Further, algae cells take 0.5 to 2 seconds to process photons of light. During this processing time, light energy that is absorbed by the algae cell is not converted to chemical energy. Dynamic mixing operations further complicate and increase costs.

In light of the above, it is an object of the present invention to provide a system and method for optimizing photoefficiency for algae cells grown in a bioreactor. For this purpose, a number of systems have been developed, such as those disclosed in co-pending U.S. Patent application Ser. No. 11/549,532 for an invention entitled "Photosynthetic Oil Production in a Two-Stage Reactor," co-pending U.S. Patent application Ser. No. 11/549,541 for an invention entitled "Photosynthetic Carbon Dioxide Sequestration and Pollution Abatement" and co-pending U.S. Patent application Ser. No. 11/549,561 for an invention entitled "Photosynthetic Oil Production with High Carbon Dioxide Utilization," which are filed concurrently herewith and assigned to the same assignee as the present invention, and are hereby incorporated by reference. Another object of the present invention is to provide a system for growing algae in a fluid stream which causes algae cells to surface for predetermined intervals of time. Still another object of the present invention is to provide a system for growing algae cells moving in a fluid stream, and to utilize simple barriers to control the flow of the fluid stream. Another object of the present invention is to provide a bioreactor system for growing algae in a fluid stream that defines a flow path for sequential movement of the algae during cell growth to and from the surface of the fluid stream. Still another object of the present invention is to create von Karman vortices in a fluid stream of algae cells to sequentially flow algae cells to the surface to receive light energy for a predetermined interval of time. Yet another object of the present invention is to provide a system and method for producing algae with high photoefficiency that is simple to implement, easy to use, and comparatively cost effective.

SUMMARY OF THE INVENTION

In accordance with the present invention, a system is provided for growing algae with improved photoefficiency. Structurally, the system includes a bioreactor formed with a conduit for growing algae cells. Further, the bioreactor has an input port for feeding a medium into the conduit and an output port for passing an effluence with algae growth from the conduit. Also, the system includes a paddlewheel, or other means, for cycling the medium through the conduit.

For purposes of the present invention, a plurality of barriers is positioned in the fluid stream. Specifically, the barriers extend between the side walls that form the conduit. Importantly, the barriers are separated by predetermined distances to sequentially create von Karman vortices in the fluid stream to repeatedly flow algae cells to the surface of the fluid stream to receive light energy for a predetermined interval of time. Von Karman vortices, or a vortex sheet, are eddies or spirals that form in a regular procession behind an obstruction in two substantially parallel rows. The vortices are staggered and each vortex is in the opposite direction from its predecessor.

Preferably, the bioreactor includes a first stage reactor and a second stage reactor. For purposes of the present invention, the first stage reactor is a continuous flow chemostat which is controlled by the paddlewheel. Further, the second stage reactor is a plug flow reactor that relies on gravity for fluid flow. In each stage, the conduit is formed by an open raceway that receives and holds a medium.

During operation, the medium is delivered into the conduit through the input port in the bioreactor. Thereafter, the paddlewheel moves the medium through the conduit at a predetermined velocity. When the medium is flowing at its predetermined velocity, the barriers cause von Karman vortices in the fluid stream to repeatedly flow algae cells to the surface of the fluid stream to receive light energy for a predetermined interval of time. In this manner, the receipt of light photons by algae cells ready to convert light energy to chemical energy is maximized.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
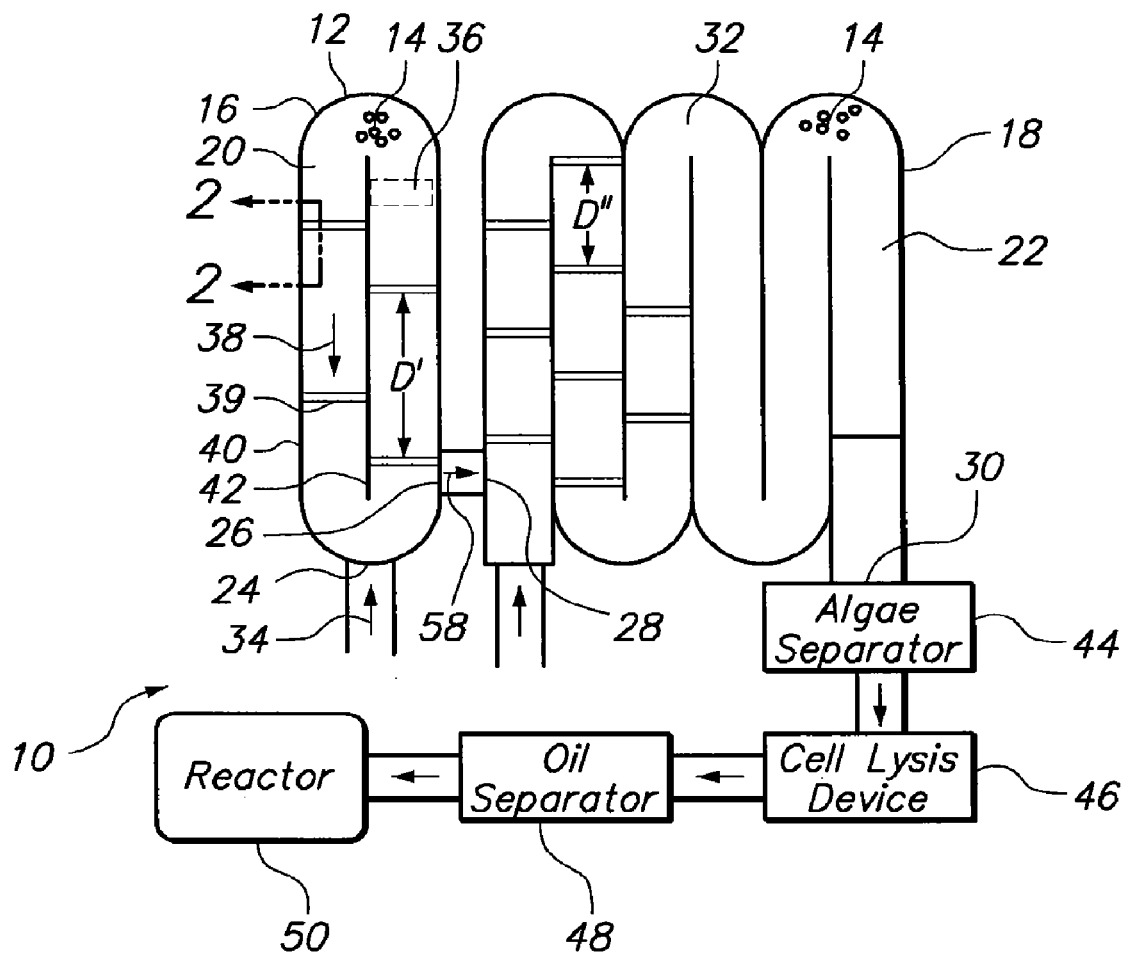
FIG. 1 is a schematic showing the system for growing algae cells with increased photoefficiency.

Referring initially to FIG. 1, a system for producing algae with improved photoefficiency is shown and generally designated 10. As shown, the system 10 includes a bioreactor 12 for growing algae cells (exemplary cells depicted at 14). Further, the bioreactor 12 is formed from a first stage reactor 16 and a second stage reactor 18. Preferably, the first stage reactor 16 is an open raceway chemostat and the second stage reactor 18 is an open raceway plug flow reactor. Each stage's reactor 16, 18 includes a conduit section 20, 22, respectively. As shown, the conduit section 20 includes an input port 24 and an output port 26. Also, the conduit section 22 includes an input port 28 and an output port 30. For purposes of the present invention, the output port 26 of the first stage reactor 16 and the input port 28 of the second stage reactor 18 are in fluid communication to create a conduit 32.

As further shown in FIG. 1, in the system 10, a medium (indicated by arrow 34) is received by the conduit 32. Further, the system 10 provides a paddlewheel 36 that is positioned in the first conduit section 20 to move the medium 34 in a fluid stream (indicated by arrow 38) at 10-100 cm per second or another predetermined fluid velocity. As also shown, a plurality of barriers 39 is positioned in the fluid stream 38 to manipulate the flow regime. Specifically, the barriers 39 extend between the sidewalls 40, 42 of the conduit 32. As shown, the barriers 39 are linear and are substantially perpendicular to the direction of fluid flow, though barriers 39 simply transverse to the fluid flow are contemplated. Further, adjacent barriers 39 are separated by a predetermined distance D that is selected to cause desired flow characteristics. As shown in FIG. 1, the distances D' in the first stage reactor 16 are different from the distances D" in the second stage reactor 18, due to the different flow rates in the stage reactors 16, 18.

Still referring to FIG. 1, it can be seen that the output port 30 is in fluid communication with an algae separator 44. Further, the algae separator 44 is connected to a cell lysis device 46. As shown, the cell lysis device 46 is in fluid communication with an oil separator 48 which, in turn, is connected to a biofuel reactor 50.

Figure 2:
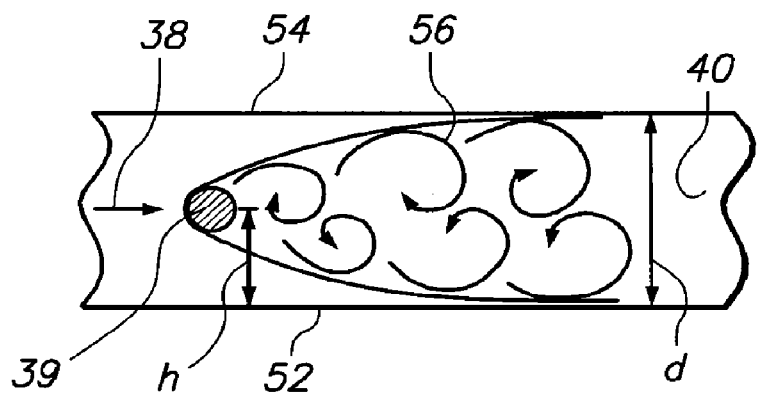
FIG. 2 is a cross sectional view taken along line 2-2 in FIG. 1, shown with arrows indicating currents in the fluid stream.

Referring to FIG. 2, the structure of a barrier 39 is more clearly illustrated. As shown, the barrier 39 in FIG. 1 has a circular cross section. For purposes of the invention, the barrier 39 may have a T-shaped, airfoil, L-shaped, rectangular, triangular, or other desired cross section. Further, the barrier 39 is shown to be about equidistant between the bottom 52 of the conduit 32 and the surface 54 of the fluid stream 38. As a result, a substantially equal volume of medium 34 may flow over and below the barrier 39. For instance, the depth, d, of the fluid stream 38 may be about 50 centimeters and the barrier 39 may be positioned at a height, h, of 25 centimeters from the bottom 52 of the conduit 32. While the barrier 39 is shown to be equidistant between the bottom 52 and the surface 541 it is contemplated that the barrier 39 may be positioned nearer the bottom 52 or nearer the surface 54, depending on the desired effect on the fluid stream 38.

In operation, the medium 34 is fed through the input port 24 into the first conduit section 20. Thereafter, the paddlewheel 36 moves the medium 34 around the first conduit section 20 at a preferred fluid flow rate of fifty centimeters per second. As the fluid stream 38 passes each barrier 39, von Karman vortices (exemplified by arrows 56) are formed in the fluid stream 38 and cause algae 14 to sequentially reach and remain near the surface 54 for predetermined intervals of time, but preferably between about 0.5 and 2 seconds. When at the surface 54, the algae 14 absorbs light photons for conversion to chemical energy.

As the fluid stream 38 circulates through the first conduit section 20, overflow (indicated by arrow 58) is received by the input port 28 of the second stage reactor 18. In the second stage reactor 18, the fluid stream 38 moves more slowly. Nevertheless, barriers 39 may be positioned in the fluid stream 38 to cause the algae cells 14 to sequentially surface to absorb light photons. When algae 14 reaches the output port 30 of the second stage reactor 18, the algae separator 44 removes the algae 14 from the fluid stream 38. Thereafter, the algae cells 14 are lysed by the cell lysis device 46 to unbind the intracellular oil from other cell matter. For purposes of the present invention, the oil and other cell matter are separated by the oil separator 48. Finally, the oil is fed to the biofuel reactor 50 which converts the oil into biofuel.

While the particular High Photoefficiency Microalgae Bioreactors as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for growing algae with improved photoefficiency which comprises:

a bioreactor formed with a conduit for growing algae cells therein, the conduit having a bottom and opposed sidewalls and the bioreactor having an input port for feeding a medium into the conduit, and having an output port for passing an effluence with algae growth from the conduit of the bioreactor;

a paddle wheel for moving the medium through the conduit of the bioreactor in a fluid stream having a surface and a predetermined fluid flow velocity; and a plurality of barriers positioned in the fluid stream, wherein each barrier extends between the opposed sidewalls of the conduit and is positioned approximately equidistant between the bottom of the conduit and the surface of the fluid stream, said barriers being separated from each other by predetermined distances to create von Karman vortices in the fluid stream to sequentially flow algae cells to the surface of the fluid stream to receive light energy for a predetermined interval of time.

2. A system as recited in claim 1 wherein the predetermined interval of time is between about 0.5 to 2.0 seconds.

3. A system as recited in claim 1 wherein the conduit is formed by two side walls, and wherein the barriers extend between the side walls transverse to the direction of the fluid flow.

4. A system as recited in claim 1 wherein the conduit includes a first section and a second section and wherein the bioreactor includes a first stage which forms the first section of the conduit and a second stage which forms the second section of the conduit, and further wherein the paddle wheel moves the medium through the first section of the conduit at a first fluid flow velocity, and wherein the barriers positioned in the first section of the conduit are separated by a first distance.

5. A system as recited in claim 4 wherein gravity moves the medium through the second section of the conduit at a second fluid flow velocity, and wherein the barriers positioned in the second section of the conduit are separated by a second distance.

6. A system as recited in claim 1 further comprising a device for processing the algae growth into biofuel.

7. A system for growing algae using improved photoefficiency which comprises:
- a conduit for growing algae cells, wherein the conduit is an open raceway with the conduit having a bottom and opposed sidewalls and having an input port for receiving a medium for growing algae, and an output port for passing an effluence with algae growth from the conduit;
- a means for moving the medium through the conduit in a fluid stream having a surface and a predetermined fluid flow velocity; and
- a plurality of barriers positioned in the fluid stream, wherein each barrier extends between the opposed sidewalls of the conduit and is positioned approximately equidistant between the bottom of the conduit and the surface of the fluid stream, for creating von Karman vortices in the fluid stream to sequentially flow algae cells to the surface of the fluid stream to receive light energy for a predetermined interval of time.

8. A system as recited in claim 7 wherein the predetermined interval of time is between about 0.5 to 2.0 seconds.

9. A system as recited in claim 7 wherein the conduit includes a first section and a second section, and wherein a paddle wheel moves the medium through the first section of the conduit at a first fluid flow velocity.

10. A system as recited in claim 7 wherein the conduit includes a first section and a second section, and wherein gravity moves the medium through the second section of the conduit at a second fluid flow velocity.

11. A system as recited in claim 7 further comprising a device for processing the algae growth into biofuel.

* * * * *

UNITED STATES PATENT AND TRADEMARK OFFICE
CERTIFICATE OF CORRECTION

PATENT NO. : 7,763,457 B2  
APPLICATION NO. : 11/549552  
DATED : July 27, 2010  
INVENTOR(S) : Eric H. Dunlop and David A. Hazlebeck It is certified that error appears in the above-identified patent and that said Letters Patent is hereby corrected as shown below:

Column 3, Line 57  
DELETE  
"541"  
INSERT  
-- 54, --

Signed and Sealed this

Sixteenth Day of November, 2010

David J. Kappos  
*Director of the United States Patent and Trademark Office*